United States Patent [19]
Rutherford et al.

[11] Patent Number: 5,747,020
[45] Date of Patent: May 5, 1998

[54] BACTERIAL TREATMENT FOR SILAGE

[75] Inventors: William Michael Rutherford, Des Moines; Mark Alan Hinds, Minburn; Scott Michael Dennis, Urbandale, all of Iowa

[73] Assignee: Pioneer Hi-Bred International, Inc., Des Moines, Iowa

[21] Appl. No.: 440,571

[22] Filed: May 15, 1995

[51] Int. Cl.$^6$ .............................. A01N 63/00; C12N 1/00; C12N 1/20
[52] U.S. Cl. ................. 424/93.45; 424/93.3; 424/93.48; 426/2; 426/53; 435/252.9; 435/857
[58] Field of Search ............................ 424/93.45, 93.48, 424/93.3; 426/2, 53; 435/252.9, 857

[56] References Cited

U.S. PATENT DOCUMENTS

| | | | |
|---|---|---|---|
| 4,842,871 | 6/1989 | Hill | 426/44 |
| 4,981,705 | 1/1991 | Tomes | 426/53 |
| 5,371,011 | 12/1994 | Bernier et al. | 435/252.4 |
| 5,451,369 | 9/1995 | Daeschel et al. | 422/28 |
| 5,458,875 | 10/1995 | Casas-Perez et al. | 424/93.45 |
| 5,480,614 | 1/1996 | Casas-Perez | 424/93.45 |
| 5,545,418 | 8/1996 | Iritani et al. | 426/53 |
| 5,547,692 | 8/1996 | Iritani et al. | 426/53 |

FOREIGN PATENT DOCUMENTS

| | | |
|---|---|---|
| 5626162 | 3/1981 | Japan . |
| 0584065 | 4/1993 | Japan . |

*Primary Examiner*—David M. Naff
*Assistant Examiner*—Deborah K. Ware
*Attorney, Agent, or Firm*—Pioneer Hi-Bred International, Inc.

[57] ABSTRACT

Silage is preserved by treatment with a small, but silage preserving effective amount of a seven strain inoculant, in which five of the strains are members of the *Lactobacillus plantarum* taxon and the remaining two strains are members of the *Enterococcus faecium* taxon. This seven strain inoculant is particularly effective in improving the aerobic stability as well as the rate and extent of digestibility of whole plant corn silage. It is also effective in improving animal milk and meat performance when animals are fed inoculated silage.

20 Claims, No Drawings

BACTERIAL TREATMENT FOR SILAGE

FIELD OF THE INVENTION

This invention relates to a method of preserving agricultural products which are used for animal feed. Specifically, this invention relates to a method of preserving silage such that the aerobic stability as well as the extent and rate of digestibility of the silage are improved. Furthermore, this invention relates to methods of increasing animal meat and milk performance.

BACKGROUND OF THE INVENTION

The use of silage additives has become a widely accepted practice throughout much of the agricultural world. In order to understand how silage additives react with silage, it may be helpful to first review the basic biochemical and microbiological changes that occur during the ensiling process. Aerobic respiration begins immediately upon chopping of silage. During this early phase, soluble carbohydrates in the plant tissue are oxidized and converted to carbon dioxide and water. This process will continue until either the oxygen level is depleted or the water soluble carbohydrates are exhausted. Under ideal conditions, with adequate packing and sealing of the ensiled material, respiration lasts only a few hours. The growth of microorganisms during this period is limited to those that are tolerant to oxygen. Typically, this includes aerobic bacteria, yeast and molds. These organisms are generally recognized as being negative to the system as they metabolize sugar to carbon dioxide, heat, and water.

Another important chemical change that occurs during this early phase is the breakdown of plant protein by plant proteases. Proteins are degraded to amino acids and further metabolized to ammonia and amines. It has been reported that up to 50% of the total proteins may be broken down during this process depending on the rate of pH decline in the silage.

Once anaerobic conditions are established, anaerobic bacteria proliferate. Enterobacteria and heterofermentative lactic acid bacteria are generally the first populations to become established. These organisms produce primarily acetic acid, ethanol, lactic acid, and carbon dioxide from the fermentation of glucose and fructose. Once the pH begins to decline, there is a marked increase in the homofermentative lactic acid bacteria population which produce primarily lactic acid. The rapid increase in the lactic acid level results in the decline of the pH to around 4. At this point, the ensiled mass will generally remain stable throughout storage if undisturbed.

In summary, when the material is initially packed in an oxygen-limiting structure, such as a covered silo, the pH is reduced, the residual oxygen is utilized and the material is said to undergo a lactic acid fermentation. The material will remain stable and can be stored for many months in this condition.

When the silage is ready to be fed, the top cover is removed and the silo is opened for feeding. The material is then exposed to air and the process is no longer anaerobic. Microflora in the silage itself or airborne contaminants can begin to oxidize the acids present. This oxidation causes a loss in mass or dry matter of the feed and thus causes feeding losses. In addition, the resultant pH and temperature increases are objectionable to the animals and the feed will be refused by the animals after it has begun to heat. The incidence of aerobic instability observed in practice depends on the rate the ensiled material is removed from the silo and the length of time that the material has been ensiled before opening. If the silage is unloaded slowly then more time is allowed on the surface of the opened silage for deterioration to occur. Longer ensiling times produce generally more stable silage as the acid concentrations are higher and all microflora populations tend to decrease. In general the silage should be stable for at least five days after opening. This will allow for adequate time for the silage to be removed.

Recently it has become known that bacterial inoculants help preserve silage, including grass silage, alfalfa silage and corn silage. For example, inoculation with lactic acid bacteria during the fermentation phase can be beneficial to the fermentation process, see for example U.S. Pat. No. 4,842,871 of Hill issued Jun. 27, 1989, as well as the literature references cited therein. For high moisture corn stability, this increase is probably due to the inoculant-enhancing the rate of anaerobic fermentation and pH decrease. This is beneficial because oxidative losses caused by aerobic pH sensitive microflora in the initial stages are thus avoided. In other silages such as whole plant corn, alfalfa, etc. the inoculant can also have beneficial effects on the digestibility of the silages by causing an increase in the availability of the fiber, and/or providing more nutrients per amount of silage at a faster rate. This is reflected in improved weight gain and feed efficiency of the animal. In dairy animals, improved digestibility leads to higher milk production, higher amounts of milk per ton of silage and improved body condition.

Accordingly, it is an objective of the present invention to develop a bacterial silage inoculant which improves aerobic stability over known inoculants.

It is a further objective of the present invention to develop a silage inoculant which increases the rate of digestibility of the silage, thereby making nutrients available to an animal sooner.

A further objective of the present invention is to develop a silage inoculant which increases the extent of digestibility of the silage, thereby providing an increase in the availability of the fiber, and/or providing more nutrients per amount of silage.

The method and manner of accomplishing each of the objectives of the present invention as well as others will become apparent from the detailed description which follows hereinafter.

SUMMARY OF THE INVENTION

In the present invention silage, including grass, alfalfa and/or whole plant corn silage, are preserved both during the initial anaerobic phase of the ensilage process and as well during the initial phases of aerobic conditions after a silo is opened. Preservation is accomplished by mixing certain facultative lactic acid bacterial microorganisms. The present inoculant improves aerobic stability of the silage, as well as meat and milk performance when the silage is fed to animals. The present inoculant further improves the extent and rate of digestibility of silage, especially whole plant corn silage. The inoculant is a combination of selected strains of *Lactobacillus plantarum* and *Enterococcus faecium*. The present inoculant is compatible with the other bacteria, and thus does not retard the ensilage process in any way. Specifically, the inoculant comprises selected strains of *Lactobacillus plantarum* "LP", LP286, LP287, LP346, LP347 and LP329, in combination with selected strains of *Enterococcus faecium* "EF", EF202 and EF301.

The present invention further provides methods of treating silage which comprises administering to the silage a small but ensilage preserving effective amount of the present inoculant prototypes. The inoculant of the present invention is particularly effective in improving the digestibility of whole plant corn silage. The present inoculant is also particularly effective in improving animal meat and milk performance if whole plant corn silage is treated with it.

DETAILED DESCRIPTION OF THE INVENTION

The term "silage" as used herein is intended to include all types of fermented agricultural products such as grass silage, alfalfa silage, whole plant corn silage, sorghum silage, fermented grains and grass mixtures, etc. All can be treated successfully with the inoculants of the present invention. The present invention is particularly effective in treating whole plant corn silage.

A surprising aspect of this invention is that only certain combinations of certain species of Lactobacillus plantarum and Enterococcus faecium will function effectively in the present invention. The addition of Lactobacillus to silage as a general matter is known, see for example U.S. Pat. No. 4,981,705, incorporated herein by reference. However, the present invention is necessarily species specific with regard to the combination of Lactobacillus plantarum and Enterococcus faecium. The present inoculant preferably comprises from about $7.5 \times 10^9$ to about $7.5 \times 10^{11}$ viable microorganisms, more preferably $7.5 \times 10^{10}$ viable microorganisms, per ton of silage of each of the following strains: LP329, LP286, LP287, LP346 and LP347; in combination with preferably from about $1.5 \times 10^9$ viable microorganisms to about $1.5 \times 10^{11}$, more preferably about $1.5 \times 10^{10}$ viable microorganisms per ton of of silage of each of the following strains: EF202 and EF301. The inoculation rate is preferably from about 10,000 to about 1,000,000 CFU per gram of forage. The LP strains are preferably included in equal proportions, comprising from about 50% to about 90%, more preferably from about 60% to about 85%, also preferably about 83% of the viable bacteria in the inoculant. The EF strains are preferably included in equal proportions, comprising from about 10% to about 50%, more preferably from about 15% to about 40%, also preferably about 17% of the viable bacteria in the inoculant. Deposits of Lactobacillus plantarum 286, Lactobacillus plantarum 287, Lactobacillus plantarum 346, Lactobacillus plantarum 347, Lactobacillus plantarum 329, Enterococcus faecium 202, and Enterococcus faecium 301 cultures are and have been maintained by Pioneer Hi-Bred International, Inc., 700 Capital Square, 400 Locust Street, Des Moines, Iowa 50309-2340 since prior to the filing date of this application.

The bacterial cultures are on deposit with the American Type Culture Collection (ATCC) and with Deutsch Sammlung von Mikroorganismen und Zellkulturen GmbH (DSM). The ATCC is at 12301 Parklawn Drive, Rockville Md., 20852 U.S.A. DSM is at Mascheroder Weg 1b, D-3300 Braunschweig, Germany. The cultures deposited with the ATCC and DSM were taken from the same culture deposits maintained at Pioneer Hi-Bred and described above.

The reference numbers are given below:

| Strain | ATCC # | Deposit Date | DSM # | Deposit Date |
|---|---|---|---|---|
| Lactobacillus plantarum LP286 | 53187 | 5-11-85 | 4784 | 9-19-88 |
| Lactobacillus plantarum | 55943 | 3-5-97 | 4787 | 9-19-88 |

-continued

| Strain | ATCC # | Deposit Date | DSM # | Deposit Date |
|---|---|---|---|---|
| LP346 Enterococcus faecium SF202 | 53519 | 7-23-86 | 4788 | 9-19-88 |
| Enterococcus faecium SF301 | 55593 | 6-21-94 | 4789 | 9-19-88 |
| Lactobacillus plantarum LP347 | 55944 | 3-5-97 | 5284 | 4-24-89 |
| Lactobacillus plantarum LP287 | 55058 | 6-5-90 | 5257 | 4-24-89 |
| Lactobacillus plantarum LP329 | 55942 | 3-5-97 | 5258 | 4-24-89 |

All restrictions imposed by the depositor on the availability of the deposited cultures to the public will be irrevocably removed upon the granting of a patent. However, applicants have no authority to waive any restrictions imposed by law on the transfer of biological material or its transportation in commerce. It should be understood that the availability of a deposit does not constitute a license to practice the subject invention in derogation of patent rights granted by government action.

The deposit will be maintained for a term of at least thirty years or at least five years after the most recent request for a sample of the deposited cultures, whichever is longer.

Applicants have satisfied all the requirements of 37 C.F.R. 1.801–1.809, including providing an indication of the viability of the sample. The deposits will be replaced should it become necessary due to inviability, contamination, or loss of capability to function in the manner described in the specification.

It is to be understood, however, that applicant's invention, while species specific, is intended to cover these species and their genetic equivalents, or the effective mutants thereof, which demonstrate the desired properties of the named species and strains. Such genetic equivalents or mutants thereof are considered to be functionally equivalent to the parent species. It is well known to those of ordinary skill in the art that spontaneous mutation is a common occurrence in microorganisms and that mutations can also be intentionally produced by a variety of known techniques. For example, mutants can be produced using chemical, radioactive, and recombinant techniques.

Regardless of the manner in which mutations or the genetic equivalents are induced, the critical issue is that they function to preserve the silage as described for the parent species and/or strain. In other words, the present invention includes mutations resulting in such minor changes as, for example, minor taxonomical alterations.

Typical compositions useful for treatment of this invention may include the present inoculants within the ranges useful for treating ensilage products, i.e. typically $10^8$–$10^{14}$ viable organisms/ton, preferably $10^9$–$10^{13}$ viable organisms/ton, more preferably $10^{11}$–$10^{12}$ organisms per ton.

The composition of the present invention can also include other common silage preservation organisms as, for example, Propionibacteria, Streptococcus, Lactococcus and Pediococcus, and certain enzymes from fungi or bacteria, providing they are in no way antagonistic to the active organisms.

Those of ordinary skill in the art will know of other suitable carriers and dosage forms, or will be able to ascertain such, using routine experimentation. Further, the administration of the various compositions can be carried out using standard techniques common to those of ordinary skill in the art, i.e. spraying, dusting, etc. For example, if a granular product is used, typically a limestone carrier is employed. A soluble product is treated with water prior to application.

The above disclosure generally describes the present invention. A more detailed understanding can be obtained by reference to the following specific examples which are provided herein for purposes of illustration only and are not intended to be limiting, unless otherwise specified.

EXAMPLES

In the examples shown in the tables below, the treatment, preparation and storage were conducted using standard procedures. The inoculants used in the silage trials were compared to a control sample which did not contain any inoculant. Treatments were applied as an aqueous solution.

Prototype combinations were applied on chopped whole plant corn in a liquid form at a rate of $1 \times 10^5$ cfu/g forage. Treated forage was divided into equal portions and packed to a standard density using a hydraulic press into 4"×14" experimental PVC silos. Silos were sealed at each end with rubber caps held tightly by metal rings. One end was fitted with a pressure release valve so that gases could escape and still maintain anaerobiosis. Experimental silos were stored at 20°–25° C. for 80–120 days prior to opening to simulate farm silo conditions.

Experimental silos were opened, silage removed into a clean container, mixed, and samples taken for microbial, chemical and digestibility analysis. The remaining silage was placed in a plastic lined polystyrene cooler, a probe placed in the center of the silage mass, and temperature measured every 3 hours for one week to determine aerobic stability. This is important because when silage is exposed to air, large losses of nutrients can occur as the result of aerobic microorganisms' consuming sugars and fermentation products in the silage. The sugars are respired to carbon dioxide and water, producing heat. Besides the loss of highly digestible portions of the silage, some aerobic microorganisms produce toxins which affect an animal's health.

Two measurements were used to determine the stability of silage upon exposure to air. The hour at which silage temperature went 1.7° C. above ambient temperature was referred to as the "rot" of the silage. It is a measure of time after the silage is exposed to air before the aerobic microorganisms start to grow causing the silage to heat. Cumulative degree days, or "cumm_dd" is the integration of the area between the actual temperature curve and a line drawn by ambient temperature. It is a measure of the total amount of heating. Elevated temperatures increase the rate and amount of protein breakdown and reduce the digestibility of nitrogen, fiber and other fractions.

Ammonia nitrogen determination was conducted using standard procedures involving dissociation of the ammonia ion by raising the pH, followed by steam distillation of the ammonia out of the silage. The amount of ammonia nitrogen is quantitatively measured by titration. The level of ammonia nitrogen is an indicator of the rate of fermentation. The faster the rate of fermentation, the lower the activity of proteolytic enzymes, thereby making more proteins available for an animal.

The fermentation endpoint measurement is pH. A satisfactory pH for whole plant corn silage is less than 4.0. As the pH decreases, proteolytic activity decreases. The pH measurements were made with an Orien® model 701A pH meter calibrated with pH 4.01 and 7.00 buffers.

To determine the extent and rate of digestibility, samples were dried and ground through a 0.5 mm Wiley® mill screen for digestibility analysis. All samples were scanned by near infrared reflectance spectroscopy (NIRS). Extremes in spectra were selected on which to run in vitro dry matter (IVDM) rates and extents of digestibility. IVDM rate of digestibility was determined using a system designed to simulate what happens in the rumen. Dried silage samples are combined with a buffer and rumen fluid containing live cellulytic microorganisms. As the cellulytic microorganisms digest the fiber in the silage sample, gas is produced. The rate of digestibility was defined as the slope of the linear portion of the curve produced by plotting gas production vs. time. It was expressed as a percent of a standard to account for the variation in microbial populations between batches of rumen fluid. A faster rate of digestibility means nutrients are being made available to the animal sooner allowing it to utilize them to produce more milk or meat.

Tables 1 and 2 report the results of the above experiments. Table 1 indicates that inoculation improves pH decline over control and increases aerobic stability when compared to uninoculated silage. The decreased pH value is advantageous in that more nutrients are preserved through acidification of the ensiled forage. Aerobic stability improvements are important because less spoilage results in an increase in the nutrients available to the animal during feeding of the ensiled material.

Table 2 indicates that the rate and extent of digestion were improved over control. A faster rate of digestibility means that nutrients would be available to an animal sooner, allowing the animal to utilize them to produce more milk or meat. One possibility of how the inoculant is causing this increase may be by changing the structure of the forage fiber, making it more available to the rumen microorganisms, which in turn convert the forage fiber to energy for use by the animal. Thus performance is improved. The extent of digestibility is also improved, indicating that the total amount of nutrients made available by digestion of the fiber is increased.

Table 3 and 4 report animal performance data from trials conducted following standard procedures. Six 2-ton silos of whole plant corn were assigned to each treatment. The treatments were control (uninoculated silage) and inoculated silage. One silo from each treatment was filled from a wagon load of forage as it was harvested. The amount of forage placed in each silo was recorded. Samples of the forage were taken as each silo was filled. Samples were also taken from each silo during the feedout period. Aerobic stabilities were conducted at the time each set of silos were opened for feeding. Ten head of steers, averaging 625 lb., were allotted by weight to each treatment for a feeding study. The cattle were fed for 42 days. The ration was 78% whole plant corn silage, 17% shelled corn and 5% supplement on a dry matter basis.

As indicated in Table 3, steers fed inoculated silage had better average daily gains and improved feed efficiencies compared to steers fed uninoculated silage. Improved average daily gain results in less time needed to raise a steer to market weight. Improved feed efficiency means that less feed is required to increase the weight of the animal. Thus, the cost of raising a given weight of beef is lower because less feed is consumed. Table 3 also indicates that dry matter recovery was greater for inoculated silage. Gain per ton of silage fed and gain per ton of forage ensiled were greater for steers fed inoculated silage. These parameters indicate that more meat can be produced from the silage fed and/or ensiled material respectively.

A dairy study was also conducted using standard procedures. Four identical bunker silos, two per treatment were each assigned to control silage or inoculated silage. Approximately 80 tons of corn forage at dent stage of maturity were ensiled into each bunker. All truck loads of forage were weighed, then unloaded alternately into the treatment bunkers. The treatments were applied in the soluble form with a backpack type sprayer. A sample from each load was obtained and composited for each bunker. Temperature probes were inserted to monitor temperature changes during the ensiling period. Nylon bags were buried toward the top and in the middle of each bunker to look at dry matter recovery ("DMR"). At feeding, a record of all silage, fed and spoiled, was kept. Samples were taken from each open bunker at designated times each week. Samples of spoiled material were also taken.

Fourteen or fifteen cows were assigned to each treatment in a continuous lactation study. Treatment groups were balanced for parity and PTA (genetic merit rating) PTA rating served as a co-variate adjustment factor. Diets consisted of 40% whole plant corn silage on a dry matter basis and was fed once daily as a total mixed ration ("TMR") (Table 3) via the Calan®/Gate System. Cows were put on the study at calving through 14 weeks. Feed refusal weights and AM-PM milk weights were obtained daily. Body weights and body condition scores were obtained at calving and weekly thereafter. Milk samples were obtained weekly for analyses of protein and fat by the Dairy Herd Improvement Association ("DHIA") lab. Samples of TMR and corn silage were obtained three times weekly and composited by calendar month. Dry matters were determined weekly on TMR's and whole plant corn silage. Samples of feed refusals were obtained twice per month for determination of dry matter.

TABLE 1

| Treatment | Dry Matter | pH | ROT | Cumm dd | Rate | Extent |
|---|---|---|---|---|---|---|
| Control | 43.38 | 3.82 | — | — | 4.37 | 4.38 |
| Inoc. Sample | 42.30 | 3.79 | — | — | 4.32 | 4.33 |
| Control | 41.52 | 3.91 | 68.00 | 196.36 | 4.34 | 4.38 |
| Inoc. Sample | 40.47 | 3.92 | 69.00 | 190.82 | 4.37 | 4.35 |
| Control | 39.07 | 3.80 | 98.60 | 137.57 | 4.37 | 4.44 |
| Inoc. Sample | 39.77 | 3.76 | 96.10 | 119.56 | 4.36 | 4.41 |

TABLE 2

| Treatment | Dry Matter | pH | ROT | Cumm dd | Rate | Extent |
|---|---|---|---|---|---|---|
| Control | 47.75 | 3.87 | — | — | 4.43 | 4.43 |
| Inoc. Sample | 44.65 | 3.83 | — | — | 4.32 | 4.31 |
| Control | 45.03 | 3.91 | 68.00 | 227.81 | 4.39 | 4.39 |
| Inoc. Sample | 43.50 | 3.90 | 79.00 | 157.97 | 4.41 | 4.38 |
| Control | 42.87 | 3.84 | 47.00 | 339.68 | 4.40 | 4.43 |
| Inoc. Sample | 43.40 | 3.81 | 46.00 | 304.62 | 4.42 | 4.44 |
| Control | 39.00 | 3.77 | — | — | 4.32 | 4.33 |
| Inoc. Sample | 39.95 | 3.76 | — | — | 4.33 | 4.36 |
| Control | 38.00 | 3.91 | 68.00 | 164.90 | 4.29 | 4.36 |
| Inoc. Sample | 37.43 | 3.94 | 59.00 | 223.66 | 4.33 | 4.33 |
| Control | 37.50 | 3.77 | 87.75 | 134.89 | 4.36 | 4.53 |
| Inoc. Sample | 37.13 | 3.75 | 81.75 | 126.85 | 4.42 | 4.57 |

TABLE 3

Feeding Performance Trial, Whole Plant Corn Silage ("WPCS"), 2-Ton Concrete Silos

| Item | Control | Inoculated Silage |
|---|---|---|
| Number of animals | 10 | 10 |
| Days on test | 42 | 42 |
| Initial wt, lb | 624.90 | 624.80 |
| Final wt, lb | 722.10 | 744.30 |
| Average daily gain, lb | 2.32 | 2.85 |
| Dry matter/lb of gain, lb | 7.28 | 6.04 |
| Dry matter intake, lb | 16.23 | 16.80 |
| WPCS dry matter, % | 36.32 | 36.68 |
| Composition of ration | | |
| WPCS, DM % | 78.00 | 78.00 |
| Shelled corn | 17.00 | 17.00 |
| Supplement, DM % | 5.00 | 5.00 |
| Dry matter recovery, % | 94.88 | 97.32 |
| Gain/ton of WPCS fed, lb | 133.30 | 157.60 |
| Gain/ton of forage ensiled, lb | 126.50 | 153.40 |
| Mean ROT value, hours | 30.90 | 28.90 |

TABLE 4

Dairy Cow Performance, WPCS Silage

| Item | Control | Inoculated Silage |
|---|---|---|
| Number of animals | 14 | 15 |
| Weeks on test | 14 | 14 |
| Weight, kg | 547.80 | 569.00 |
| Dry matter intake, kg/d | 16.99 | 16.57 |
| Milk production, kg/d | 31.20 | 32.90 |
| Fat, % | 3.59 | 3.35 |
| 3.5% fat corrected milk, kg/d | 31.30 | 31.90 |
| Daily protein production, kg/d | .95 | 1.00 |
| Body condition score, (1–5 point scale) | 3.22 | 3.35 |
| WPCS dry matter, % | 25.38 | 26.15 |
| Composition of ration, % DM | | |
| Grain mix | 45.00 | 45.00 |
| WPCS | 40.00 | 40.00 |
| Whole corn seed | 10.00 | 10.00 |
| Alfalfa hay | 5.00 | 5.00 |
| Bunker dry matter recovery, % | 83.20 | 89.40 |
| Bag dry matter recovery, % | | |
| Top | 80.20 | 92.90 |
| Middle | 98.40 | 97.70 |
| Milk/ton of WPCS fed, lb | 2337 | 2517 |
| Mean ROT value, hours | 42 | 23 |

What is claimed is:

1. A silage inoculant comprising:
 a) the microorganism *Lactobacillus plantarum* 286 having ATCC Accession No. 53187, or a mutant strain thereof possessing all of the identifying characteristics of the microorganism;
 b) the microorganism *Lactobacillus plantarum* 287 having ATCC Accession No. 55058, or a mutant strain thereof possessing all of the identifying characteristics of the microorganism;
 c) the microorganism *Lactobacillus plantarum* 346 having ATCC Accession No. 55943, or a mutant strain thereof possessing all of the identifying characteristics of the microorganism;
 d) the microorganism *Lactobacillus plantarum* 347 having ATCC Accession No. 55944, or a mutant strain thereof possessing all of the identifying characteristics of the microorganism;

e) the microorganism *Lactobacillus plantarum* 329 having ATCC Accession No. 55942, or a mutant strain thereof possessing all of the identifying characteristics of the microorganism;

f) the microorganism *Enterococcus faecium* 346 having ATCC Accession No. 53519, or a mutant strain thereof possessing all of the identifying characteristics of the microorganism; and g) the microorganism *Enterococcus faecium* 301 having ATCC Accession No. 55593, or a mutant strain thereof possessing all of the identifying characteristics of the microorganism.

2. The inoculant of claim 1 wherein said inoculant comprises *Lactobacillus plantarum* 286, *Lactobacillus plantarum* 287, *Lactobacillus plantarum* 346, *Lactobacillus plantarum* 347 and *Lactobacillus plantarum* 329, each in equal proportions, together comprising from about 50% to about 90% of all viable bacteria; and *Enterococcus faecium* 202 and *Enterococcus faecium* 301, each in equal proportions, together comprising from about 10% to about 50% of all viable bacteria.

3. The inoculant of claim 3 wherein said inoculant comprises *Lactobacillus plantarum* 286, *Lactobacillus plantarum* 287, *Lactobacillus plantarum* 346, *Lactobacillus plantarum* 347 and *Lactobacillus plantarum* 329, each in equal proportions, together comprising from about 60% to about 85%, of all viable bacteria; and *Enterococcus faecium* 202 and *Enterococcus faecium* 301 each in equal proportions, together comprising from about 15% to about 40% of all viable bacteria.

4. The inoculant of claim 3 wherein said inoculant comprises *Lactobacillus plantarum* 286, *Lactobacillus plantarum* 287, *Lactobacillus plantarum* 346, *Lactobacillus plantarum* 347 and *Lactobacillus plantarum* 329, each in equal proportions, together comprising 83% of all viable bacteria; and *Enterococcus faecium* 202 and *Enterococcus faecium* 301, each in equal proportions, together comprising 17% of all viable bacteria.

5. A method of preserving silage, said method comprising treating silage with an inoculant comprising:

a) the microorganism *Lactobacillus plantarum* 286 having ATCC Accession No. 53187, or a mutant strain thereof possessing all of the identifying characteristics of the microorganism;

b) the microorganism *Lactobacillus plantarum* 287 having ATCC Accession No. 55058, or a mutant strain thereof possessing all of the identifying characteristics of the microorganism;

c) the microorganism *Lactobacillus plantarum* 346 having ATCC Accession No. 55943, or a mutant strain thereof possessing all of the identifying characteristics of the microorganism;

d) the microorganism *Lactobacillus plantarum* 347 having ATCC Accession No. 55944, or a mutant strain thereof possessing all of the identifying characteristics of the microorganism;

e) the microorganism *Lactobacillus plantarum* 329 having ATCC Accession No. 55942, or a mutant strain thereof possessing all of the identifying characteristics of the microorganism;

f) the microorganism *Enterococcus faecium* 202 having ATCC Accession No. 53519, or a mutant strain thereof possessing all of the identifying characteristics of the microorganism; and g) the microorganism *Enterococcus faecium* 301 having ATCC Accession No. 55593, or a mutant strain thereof possessing all of the identifying characteristics of the microorganism.

6. The method of claim 5 wherein said inoculant comprises *Lactobacillus plantarum* 286, *Lactobacillus plantarum* 287, *Lactobacillus plantarum* 346, *Lactobacillus plantarum* 347 and *Lactobacillus plantarum* 329 each in equal proportions, together comprising from about 60% to about 85% of all viable bacteria; and *Enterococcus faecium* 202 and *Enterococcus faecium* 301 each in equal proportions, together comprising from about 15% to about 40% of all viable bacteria.

7. The method of claim 6 wherein the silage preserved is whole plant corn silage.

8. The method of claim 7 wherein the silage contains from about $10^8$ to about $10^{14}$ viable organisms per ton.

9. The method of claim 8 wherein the silage contains from about $10^9$ to about $10^{13}$ viable organisms per ton.

10. A method of improving animal meat and milk performance said method comprising feeding an animal silage treated with an inoculant comprising:

a) the microorganism *Lactobacillus plantarum* 286 having ATCC Accession No. 53187, or a mutant strain thereof possessing all of the identifying characteristics of the microorganism;

b) the microorganism *Lactobacillus plantarum* 287 having ATCC Accession No. 55058, or a mutant strain thereof possessing all of the identifying characteristics of the microorganism;

c) the microorganism *Lactobacillus plantarum* 346 having ATCC Accession No. 55943, or a mutant strain thereof possessing all of the identifying characteristics of the microorganism;

d) the microorganism *Lactobacillus plantarum* 347 having ATCC Accession No. 55944, or a mutant strain thereof possessing all of the identifying characteristics of the microorganism;

e) the microorganism *Lactobacillus plantarum* 329 having ATCC Accession No. 55942, or a mutant strain thereof possessing all of the identifying characteristics of the microorganism;

f) the microorganism *Enterococcus faecium* 202 having ATCC Accession No. 53519, or a mutant strain thereof possessing all of the identifying characteristics of the microorganism; and g) the microorganism *Enterococcus faecium* 301 having ATCC Accession No. 55593, or a mutant strain thereof possessing all of the identifying characteristics of the microorganism.

11. The method of claim 10 wherein said inoculant comprises *Lactobacillus plantarum* 286, *Lactobacillus plantarum* 287, *Lactobacillus plantarum* 346, *Lactobacillus plantarum* 347 and *Lactobacillus plantarum* 329, each in equal proportions, together comprising from about 60% to about 85% of all viable bacteria; and *Enterococcus faecium* 202 and *Enterococcus faecium* 301 each in equal proportions, together comprising from about 15% to about 40% of all viable bacteria.

12. The method of claim 11 wherein the silage preserved is whole plant corn silage.

13. The method of claim 12 wherein the silage contains from about $10^8$ to about $10^{14}$ viable organisms per ton.

14. The method of claim 15 wherein the silage contains from about $10^9$ to about $10^{13}$ viable organisms per ton.

15. The method of claim 16 wherein the silage contains about $10^{11}$ to about $10^{12}$ viable organisms per ton.

16. A method of improving the digestibility of silage, said method comprising treating silage with an inoculant comprising:

a) the microorganism *Lactobacillus plantarum* 286 having ATCC Accession No. 53187, or a mutant strain thereof possessing all of the identifying characteristics of the microorganism;

b) the microorganism *Lactobacillus plantarum* 287 having ATCC Accession No. 55058, or a mutant strain thereof possessing all of the identifying characteristics of the microorganism;

c) the microorganism *Lactobacillus plantarum* 346 having ATCC Accession No. 55943, or a mutant strain thereof possessing all of the identifying characteristics of the microorganism;

d) the microorganism *Lactobacillus plantarum* 347 having ATCC Accession No. 55944, or a mutant strain thereof possessing all of the identifying characteristics of the microorganism;

e) the microorganism *Lactobacillus plantarum* 329 having ATCC Accession No. 55942, or a mutant strain thereof possessing all of the identifying characteristics of the microorganism;

f) the microorganism *Enterococcus faecium* 202 having ATCC Accession No. 53519 or a mutant strain thereof possessing all of the identifying characteristics of the microorganism; and g) the microorganism *Enterococcus faecium* 301 having ATCC Accession No. 55593, or a mutant strain thereof possessing all of the identifying characteristics of the microorganism.

17. The method of claim 16 wherein said inoculant comprises *Lactobacillus plantarum* 286, *Lactobacillus plantarum* 287, *Lactobacillus plantarum* 346, *Lactobacillus plantarum* 347 and *Lactobacillus plantarum* 329, each in equal proportions, together comprising from about 60% to about 85% of all viable bacteria; and *Enterococcus faecium* 202 and *Enterococcus faecium* 301, each in equal proportions, together comprising from about 15% to about 40% of all viable bacteria.

18. The method of claim 17 wherein the silage preserved is whole plant corn silage.

19. The method of claim 18 wherein the silage contains from about $10^8$ to about $10^{13}$ viable organisms per ton.

20. The method of claim 19 wherein the silage contains from about $10^9$ to about $10^{11}$ viable organisms per ton.

* * * * *

UNITED STATES PATENT AND TRADEMARK OFFICE
CERTIFICATE OF CORRECTION

| | | |
|---|---|---|
| PATENT NO. | : 5,747,020 | Page 1 of 1 |
| DATED | : May 5, 1998 | |
| INVENTOR(S) | : William Michael Rutherford, Mark Alan Hinds and Scott Michael Dennis | |

It is certified that error appears in the above-identified patent and that said Letters Patent is hereby corrected as shown below:

Column 9,
Line 5, should read:
-- f) the microorganism *Enterococcus faecium* 202 having --.

Signed and Sealed this

Twenty-seventh Day of December, 2005

JON W. DUDAS
*Director of the United States Patent and Trademark Office*